United States Patent [19]
Häfele et al.

[11] Patent Number: 5,616,028
[45] Date of Patent: Apr. 1, 1997

[54] DENTAL-JET DEVICE AND MOUTHPIECE FOR A DENTAL-JET DEVICE

[75] Inventors: Peter Häfele, Unterbergen; Ernst Poganitsch, Klagenfurt, both of Austria

[73] Assignee: U.S. Philips Corporation, New York, N.Y.

[21] Appl. No.: 491,010

[22] Filed: Jun. 15, 1995

[30] Foreign Application Priority Data

Jun. 21, 1994 [AT] Austria .................. 1222/94

[51] Int. Cl.$^6$ .................. A61C 17/02
[52] U.S. Cl. .................. 433/80
[58] Field of Search .................. 433/80, 88, 82, 433/85, 87, 84, 89

[56] References Cited

U.S. PATENT DOCUMENTS

| | | | |
|---|---|---|---|
| 4,975,054 | 12/1990 | Esrock | 433/80 |
| 5,192,206 | 3/1993 | Davis et al. | 433/80 |
| 5,236,356 | 8/1993 | Davis et al. | 433/80 |

FOREIGN PATENT DOCUMENTS

| | | | |
|---|---|---|---|
| 3526579 | 7/1986 | Germany . | |
| 0665347 | 5/1988 | Switzerland | 433/80 |

*Primary Examiner*—Edgar S. Burr
*Assistant Examiner*—Dave A. Ghatt
*Attorney, Agent, or Firm*—Ernestine C. Bartlett

[57] ABSTRACT

A dental-jet device (1) is provided comprising a grip member (4) and at least one mouthpiece having a tubular part (8) and a nozzle head (7) mounted on the tubular part (8) so as to be rotatable about an axis of rotation (15) and sealed relative to the tubular part (8) by a seal (21), which nozzle head has at least one central jet orifice (16) and a plurality of peripheral jet orifices (17), the tubular part (8) has a single tubular-part outlet (23) which communicates with its fluid channel (9) and which is off-centered from the axis of rotation (15), and the nozzle head (17) has only two nozzle-head inlets (24, 25), which are off-centered from the axis of rotation (15) and which are sealed from one another by means of a second seal (26) acting between the tubular part (8) and the nozzle head (7), one nozzle-head inlet (24) connecting the tubular-part outlet (23) to the central-jet orifice (16) in the central-jet position and the other nozzle-head inlet (25) connecting the tubular-part outlet (23) to the peripheral-jet orifices (17) in the peripheral-jet position.

4 Claims, 3 Drawing Sheets

DENTAL-JET DEVICE AND MOUTHPIECE FOR A DENTAL-JET DEVICE

FIELD OF THE INVENTION

The invention relates to a dental-jet device comprising a grip member and at least one mouthpiece, which mouthpiece is connectible to the grip member and comprises a tubular part having a fluid channel and a nozzle head mounted on the tubular part at the location of the free end of said tubular part so as to be rotatable about an axis of rotation between a central-jet position and a peripheral-jet position, which nozzle head has at least one central jet orifice and a plurality of peripheral jet orifices, a ring-shaped seal being interposed between the tubular part and the nozzle head in order to preclude an undesirable water discharge to the exterior of the mouthpiece.

The invention further relates to a mouthpiece for a dental-jet device, which mouthpiece comprises a tubular part having a fluid channel and a nozzle head mounted on the tubular part at the location of the free end of said tubular part so as to be rotatable about an axis of rotation between a central-jet position and a peripheral-jet position, which nozzle head has at least one central jet orifice and a plurality of peripheral jet orifices, a ring-shaped seal being interposed between the tubular part and the nozzle head in order to preclude an undesirable water discharge to the exterior of the mouthpiece.

BACKGROUND OF THE INVENTION

A dental-jet device of the type defined in the first paragraph and a mouthpiece of the type defined in the second paragraph are known, for example from DE-A1-35 26 579. In the known dental-jet device and the known mouthpiece the tubular part has a widened end portion, which widened end portion engages with an intermediate portion of the tubular part. The intermediate portion has a plurality of flow channels, in and also has mounted therein a jet insert of the tubular part. The insert has ports for the supply of fluid, i.e. of water, to the peripheral-jet orifices in the nozzle head and has a passage for the supply of fluid, i.e. of water, to a central-jet orifice in the nozzle head. The jet insert of the tubular part has a surface transverse to the axis of rotation of the nozzle head which simply engages with a nozzle-head surface transverse to the axis of rotation of the nozzle head. As a result of this construction, water undesirably discharges from the peripheral-jet orifices when the nozzle head is in its central-jet position and consequently loss of volume and loss of pressure occur in the water jet emerging from the central-jet orifice. Apart from this undesired property of the known dental-jet device and the known mouthpiece, it is also unfavourable that the known mouthpiece of the known dental-jet device is of a comparatively intricate construction, comprising a comparatively large number of parts.

SUMMARY OF THE INVENTION

It is an object of the invention to mitigate the above problems and to improve a dental-jet device of the type defined in the first paragraph and a mouthpiece of the type defined in the second opening paragraph by simple means and in a simple manner, in such a way that no undesirable fluid discharge from any of the jet orifices of the nozzle head is possible and the nozzle head is of a particularly simple and reliable construction.

To this end, according to the invention, a dental-jet device of the type defined in the first paragraph is characterized in that the tubular part has a single tubular-part outlet which communicates with the fluid channel of the tubular part and which is off-centered from the axis of rotation of the nozzle head, and in that the nozzle head has only two nozzle-head inlets, which are off-centered from the axis of rotation of the nozzle head. The two nozzle-head inlets are sealed from one another by means of a second ring-shaped seal acting between the tubular part and the nozzle head. Additionally, the first nozzle-head inlet is in fluid-transmitting communication with the tubular-part outlet in the central-jet position of the nozzle head, and the second nozzle-head inlet is in fluid-transmitting communication with the tubular-part outlet in the peripheral-jet position of the nozzle head. Also, the first nozzle-head inlet is in fluid-transmitting communication with the at least one central-jet orifice of the nozzle head and the second nozzle-head inlet with the peripheral-jet orifices of the nozzle head. In this way it is achieved by very simple means that the fluid supply to the at least one central-jet orifice and the fluid supply to the peripheral-jet orifices of the nozzle head are correctly isolated from one another, so that no undesirable fluid discharge from any of the jet orifices of the nozzle head is possible. Moreover, it provides a very simple construction of the mouthpiece of a dental-jet device in accordance with the invention.

An especially preferred embodiment of a dental-jet device in accordance with the invention is characterized in that the second seal is arranged between surfaces of the tubular part and of the nozzle head, which surfaces extend parallel to the axis of rotation of the nozzle head, and in that the ring plane of the second seal is inclined relative to the axis of rotation of the nozzle head. This is advantageous in order to minimize the dimension of the nozzle head of the mouthpiece as small as possible in a direction transverse to the axis of rotation of the nozzle head. It is also advantageous because the forces between the tubular part and the nozzle head caused by the second ring-shaped seal between the surfaces of the tubular part and the nozzle head and caused by the fluid pressure are taken up by the areas of the tubular part and of the nozzle head which are coaxial with the axis of rotation of the nozzle head.

According to the invention a mouthpiece of the type defined in the second paragraph is characterized in that the tubular part has a single tubular-part outlet which communicates with the fluid channel of the tubular part and which is off-centered from the axis of rotation of the nozzle head, and in that the nozzle head has only two nozzle-head inlets, which are off-centered from the axis of rotation of the nozzle head and which are sealed from one another by means of a second ring-shaped seal acting between the tubular part and the nozzle head. Additionally, the first nozzle-head inlet is in fluid-transmitting communication with the tubular-part outlet in the central-jet position of the nozzle head and the second nozzle-head inlet is in fluid-transmitting communication with the tubular-part outlet in the peripheral-jet position of the nozzle head. Also, the first nozzle-head inlet is in fluid-transmitting communication with the at least one central-jet orifice of the nozzle head and the second nozzle-head inlet with the peripheral-jet orifices of the nozzle head. In this way it is achieved by very simple means that the fluid supply to the at least one central-jet orifice and the fluid supply to the peripheral-jet orifices of the nozzle head are effectively isolated from one another, so that no undesirable fluid discharge from any of the jet orifices of the nozzle head is possible. Moreover, it provides a very simple construction of the mouthpiece.

An especially preferred embodiment of a mouthpiece in accordance with the invention is characterized in that the second seal is arranged between surfaces of the tubular part and of the nozzle head, which surfaces extend parallel to the axis of rotation of the nozzle head, and in that the ring plane of the second seal is inclined relative to the axis of rotation of the nozzle head. This is advantageous in order to minimize the dimension of the nozzle head of the mouthpiece as small as possible in a direction transverse to the axis of rotation of the nozzle head. It is also advantageous because the forces between the tubular part and the nozzle head caused by the second ring-shaped seal between the surfaces of the tubular part and the nozzle head and caused by the fluid pressure are taken up by the areas of the tubular part and of the nozzle head which are coaxial with the axis of rotation of the nozzle head.

BRIEF DESCRIPTION OF THE DRAWINGS

The invention will now be described in more detail with reference to the drawings, which show two exemplary embodiments to which the invention is not limited.

DETAILED DESCRIPTION OF THE PREFERRED EMBODIMENTS

Figure 1:
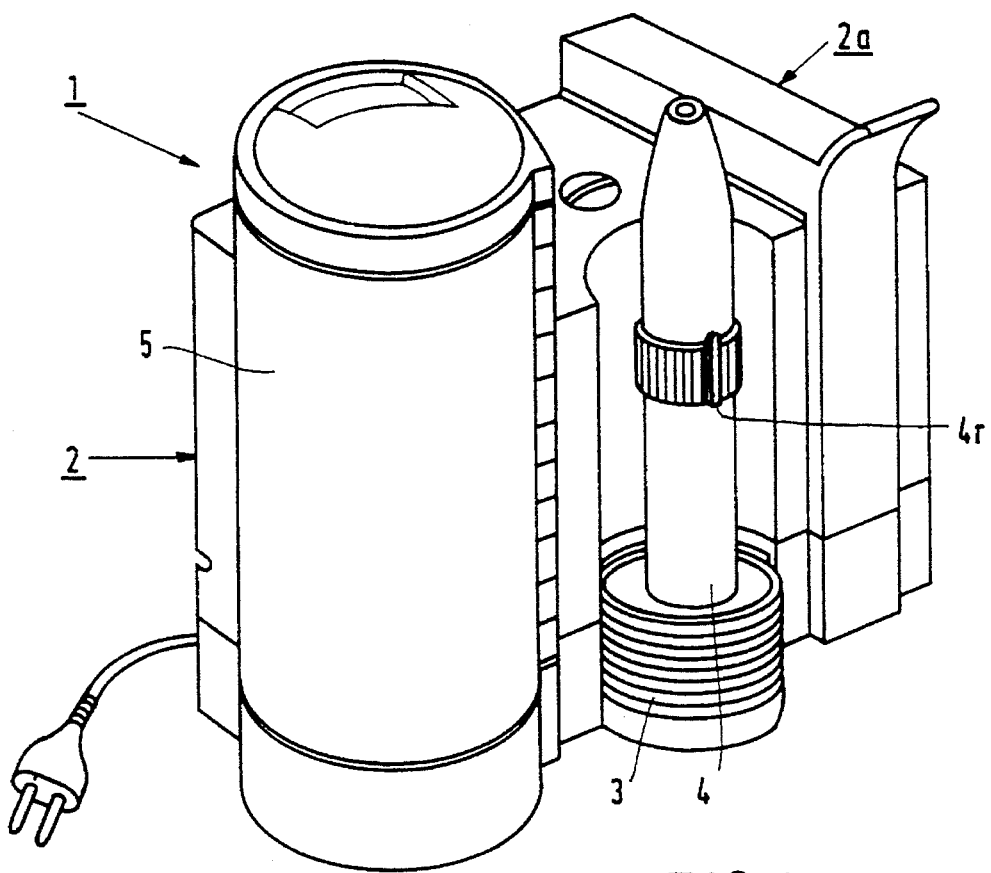
FIG. 1 is a diagrammatic oblique view of a dental-jet device comprising a basic appliance and a grip member connected to the basic appliance via a tube, the basic appliance comprising an arrangement for holding mouthpieces, which can each be fitted onto the grip member.

FIG. 1 shows a dental-jet device 1, which comprises a basic appliance 2 and a grip member 4 connected to the basic appliance 2 via a flexible tube 3. A fluid container 5 is placed on the basic appliance 2, which comprises a motor-driven pump means by which a fluid, for example water, can be pumped from the fluid container to the grip member 4 via the tube 3. The grip member 4 can be provided with different mouthpieces, as is shown for a mouthpiece 6 in FIG. 2. The fluid pumped to the grip member 4 is fed to the mouthpiece 6 to form a jet for cleaning the teeth and gums and for gum massage. In order to select a desired fluid flow the grip member 4 has an adjustment ring 4r. A fluid-flow control means provided in the grip member 6 is adjustable by turning the adjustment ring 4r. Instead of pure water the fluid container 5 may be filled with water with an additive or with another liquid oral or dental care agent. To hold different mouthpieces 6 the basic appliance 2 comprises a holder 2a, which is shown in its closed position in FIG. 1.

Figure 2:
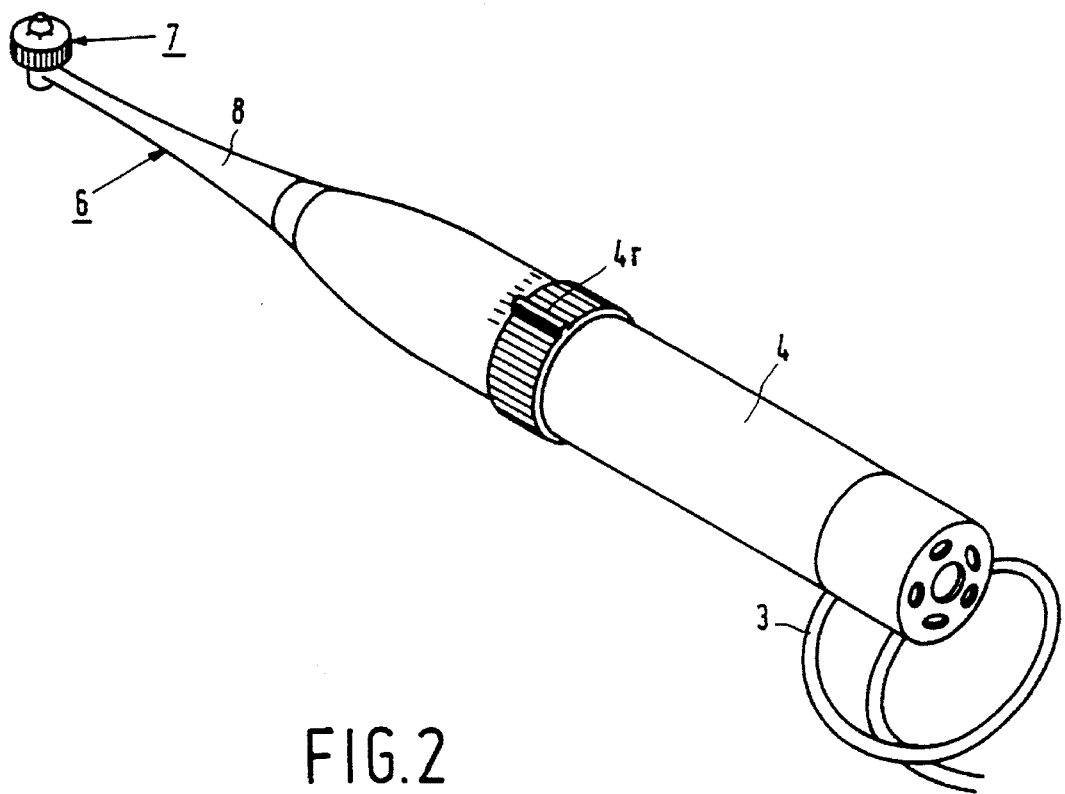
FIG. 2 is a diagrammatic oblique view of the grip member of the dental cleaning device shown in FIG. 1, a mouthpiece being fitted onto the grip member and comprising at its free end a nozzle head which is rotatable between a central-jet position and a peripheral-jet position.
Figure 3:
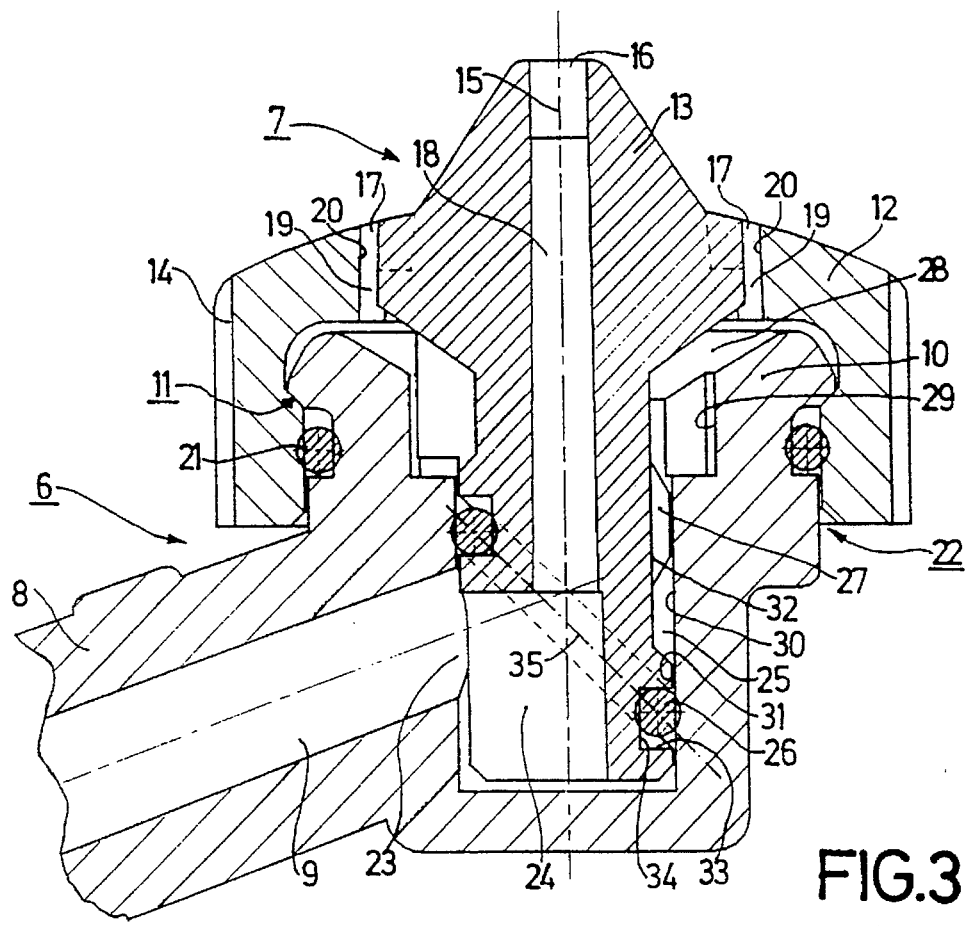
FIG. 3 is a cross-sectional view of the end of the mouthpiece shown in FIG. 2, the nozzle head being in its central-jet position.
Figure 4:
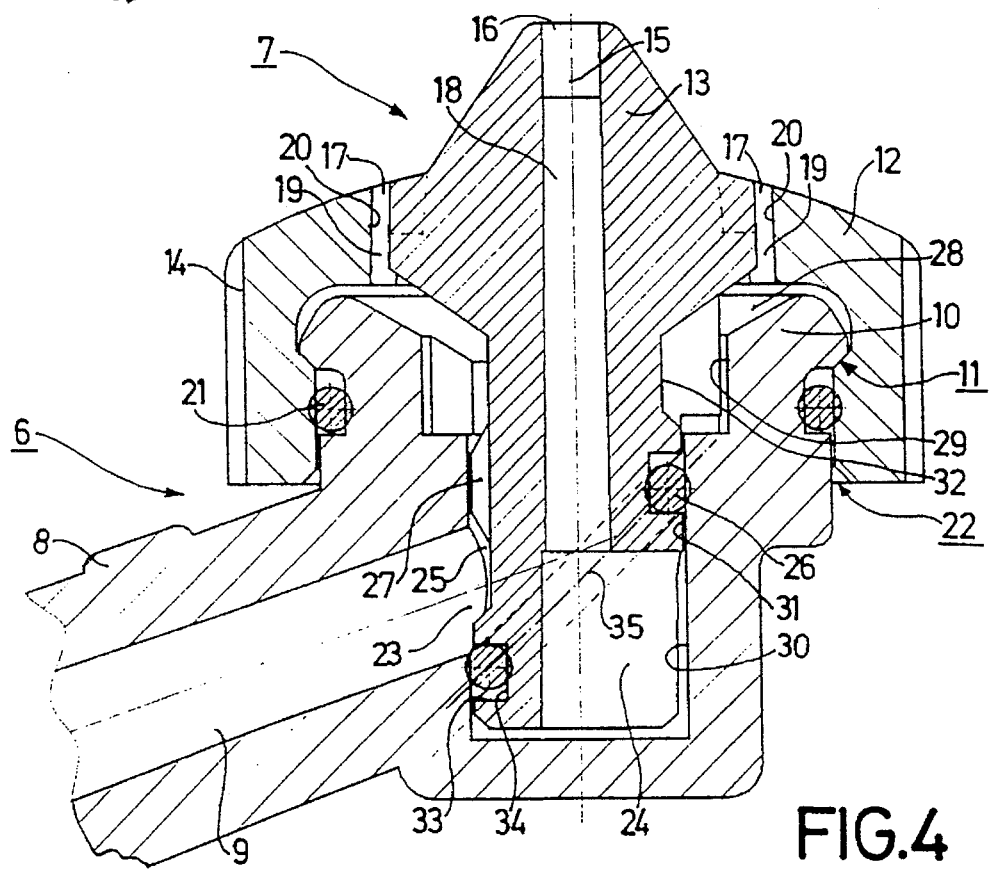
FIG. 4, in the same way as FIG. 3, shows the nozzle head in its peripheral-jet position.

As is shown in FIGS. 2, 3 and 4, the mouthpiece 6 comprises a tubular part 8 with a fluid channel 9. The mouthpiece 6 further comprises the nozzle head 7, which is rotatably mounted at the free end 10 of the tubular part 8 by means of a coupling 11. In the present case the nozzle head 7, which in the same way as the tubular part 8 is made of a plastic material, is made up of two parts for reasons of molding technology, but it may alternatively consist of a single part. The nozzle head 7 comprises a substantially hollow cylindrical outer part 12 in which an inner part 13 is fitted so as to be locked against rotation relative to the outer part 12. The outer part 12 has a knurled circumferential portion 14 to facilitate rotation of the nozzle head 7 relative to the tubular part 8. The nozzle head 7 is rotatable relative to the tubular part 8 about an axis of rotation 15 through an angular range of approximately 180° between a central-jet position shown in FIG. 3 and a peripheral-jet position shown in FIG. 4.

The nozzle head 7 has a central-jet orifice 16, which is coaxial with the axis of rotation 15, and a plurality of peripheral-jet orifices 17, which are off-centered in relation to the axis of rotation 15. For example, eight of such peripheral-jet orifices 17 may be spaced at equal angles from one another. The central-jet orifice 16 is situated at the end of a central-jet channel 18 traversing the inner part 13 and the peripheral-jet orifices 17 are situated at the ends of peripheral-jet channels 19, which are formed by ducts in the peripheral area of the inner part 13 and which are bounded by the inner surface 20 of the outer part 12. However, alternatively the nozzle head 7 may have two or three central-jet orifices, which are slightly off-centered from the axis of rotation 15.

A first ring-shaped rubber seal 21 is interposed between the tubular part 8 and the nozzle head 7 in order to preclude an undesirable water discharge to the exterior of the mouthpiece 6 in the transitional area between the tubular part 8 and the nozzle head 7.

As is shown in FIGS. 3 and 4, the tubular part 8 of the mouthpiece 6 has a single tubular-part outlet 23, which communicates with the fluid channel 9 of the tubular part 8 and which is off-centered from the axis of rotation 15 of the nozzle head 7. The nozzle head 7 has only two nozzle-head inlets 24 and 25, which are off-centered from the axis of rotation 15 of the nozzle head 7. The two nozzle-head inlets 24 and 25 are sealed from one another by means of a second ring-shaped seal 26 interposed between the tubular part 8 and the nozzle head 7. In the central-jet position of the nozzle head 7 a first nozzle-head inlet 24 of the two nozzle-head inlets 24 and 25 is in fluid-transmitting communication with the tubular-part outlet 23, as is shown in FIG. 3. In the peripheral-jet position of the nozzle head 7 the second nozzle-head inlet 25 is in fluid-transmitting communication with the tubular-part outlet 23, as is shown in FIG. 4. The first nozzle-head inlet 24 communicates with the central-jet orifice 16 via the central-jet channel 18. The second nozzle-head inlet 25 is in fluid-transmitting communication with the peripheral-jet channels 19 and, consequently, with the peripheral jet orifices 17 of the nozzle head 7 via a substantially cylindrical first channel portion 27, which is situated between the free end 10 of the tubular part 8 and the inner part 13 of the nozzle head 7, and a substantially frustoconical second channel portion 28, which adjoins the first channel portion 27 and which is also situated between the free end 10 of the tubular part 8 and the inner part 13 of the nozzle head 7.

In the case of the tubular part 8 and the nozzle head 7 as shown in FIGS. 3 and 4, the free end 10 has a hollow cylindrical shape which is substantially coaxial with the axis of rotation 15. The portion of the inner part 13 which extends into the interior of the hollow cylindrical free end 10 is essentially bounded by two cylindrical surfaces 31 and 32 which extend parallel to the axis of rotation 15 of the nozzle head 7. In the part of the cylindrical surface 31 which is situated substantially between two planes which are inclined relative to the axis of rotation 15 of the nozzle head 7, the inner part 13 has a groove 33, which at the bottom side is bounded by a cylindrical surface 34 which also extends parallel to the axis of rotation 15 of the nozzle head 7. The second ring-shaped seal 26 is fitted in this groove 33. The second ring-shaped seal 26 thus lies between surfaces 30 and 34 of the tubular part 8 and the nozzle head 7, which surfaces extend parallel to the axis of rotation 15 of the nozzle head 7. Owing to the shape of the cylindrical surface 31 and the groove 33 the ring plane 35 of the second ring-shaped seal 26 is inclined relative to the axis of rotation 15 of the nozzle head 7.

In the dental-jet device described above with reference to FIGS. 1 to 4, it is achieved by very simple means that the fluid supply to the central jet orifice and the fluid supply to the peripheral jet orifices of the nozzle head are effectively isolated from one another, so that depending on the rotary position of the nozzle head relative to the tubular part of the mouthpiece, fluid is supplied to either only the central jet orifice or only the peripheral jet orifices and no undesirable fluid discharge from any of the non-activated jet orifices is possible. Moreover, the dental-jet device described above has a very simple construction of the mouthpiece and the nozzle head, the nozzle head having advantageously small radial dimensions owing to the hollow cylindrical shape of the free end portion of the tubular part. The hollow cylindrical shape of the free end portion of the tubular part and the corresponding shape of the nozzle head further have the advantage that the forces between the tubular part and the nozzle head caused by the second ring-shaped seal between the surfaces of the tubular part and the nozzle head and also by the fluid pressure are taken up by the areas of the tubular part and of the nozzle head which are coaxial with the axis of rotation of the nozzle head, so that these forces exert hardly any load on the coupling means for coupling the nozzle head to the tubular part.

Figure 5:
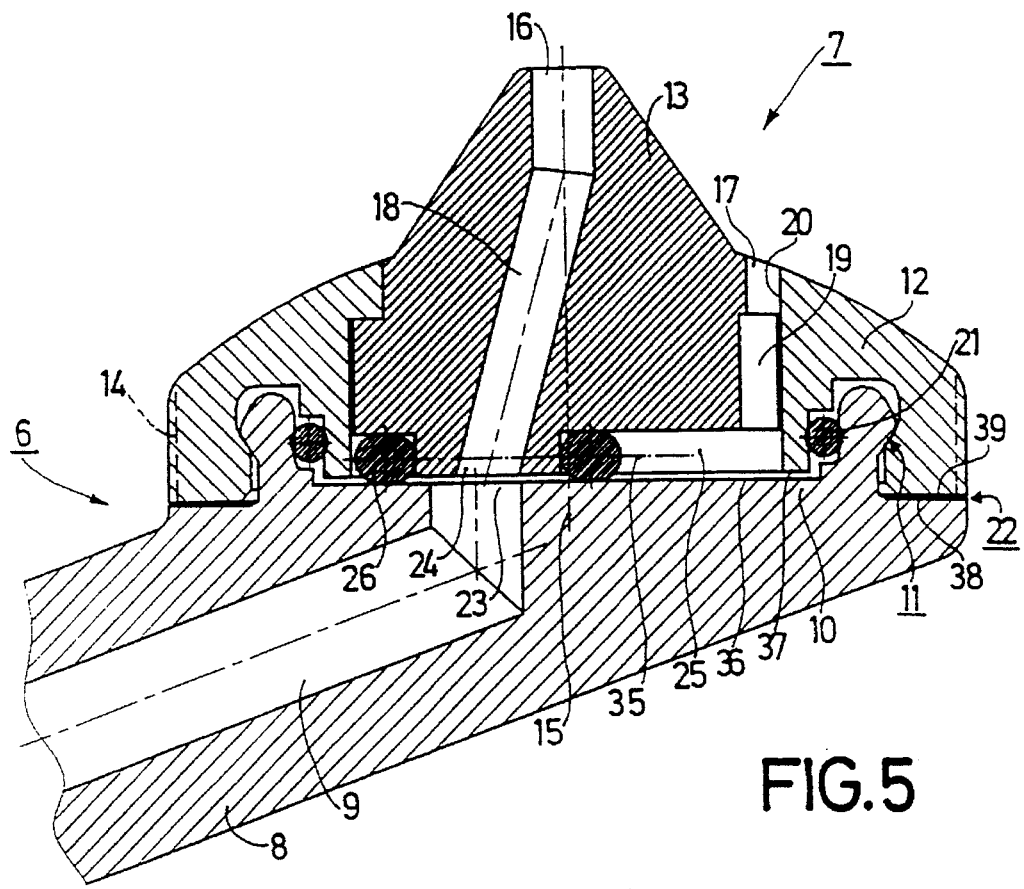
FIG. 5, in the same way as FIGS. 3 and 4, shows the end of a mouthpiece in a second embodiment of the invention, with a nozzle head in its central-jet position.
Figure 6:
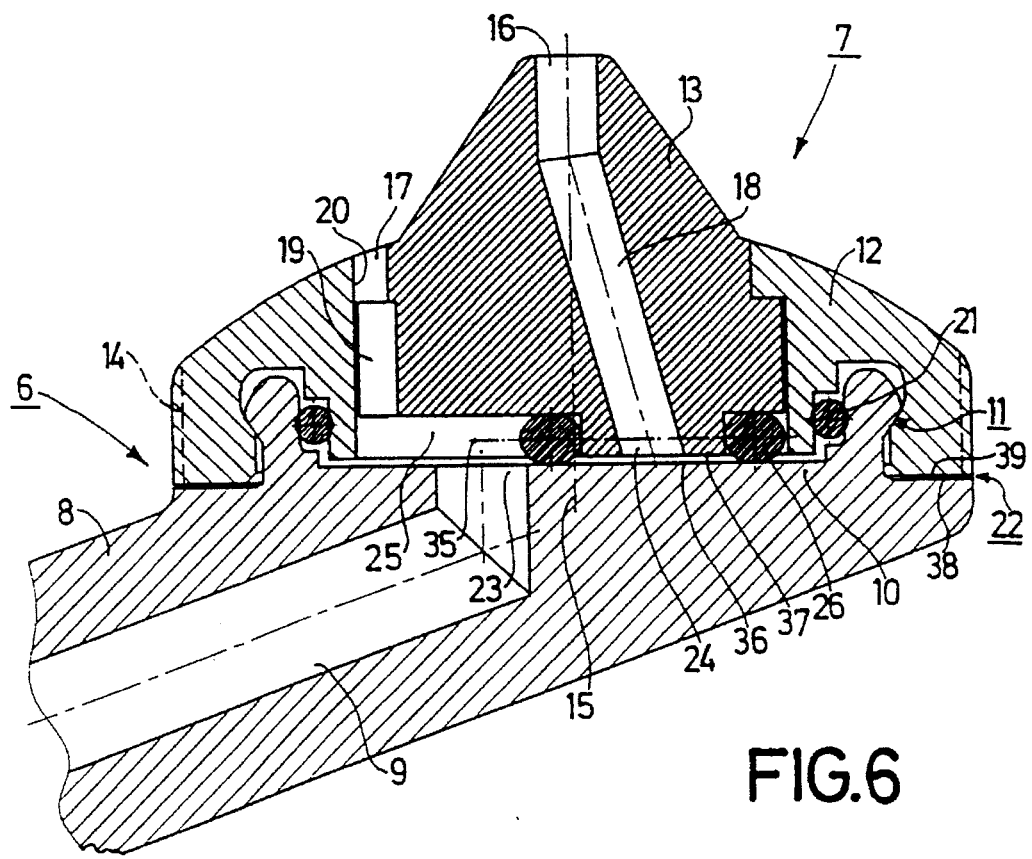
FIG. 6, in the same way as FIGS. 3, 4 and 5, shows the end of the mouthpiece of FIG. 5, the nozzle head being in its peripheral-jet position.

FIGS. 5 and 6 show a part of the mouthpiece 6 of a dental-jet device in accordance with a second embodiment of the invention. In this mouthpiece 6 the tubular part 8, with its free end 10, and the nozzle head 7 essentially adjoin one another with surfaces 36, 37 and 38, 39 which extend perpendicularly to the axis of rotation 15 of the nozzle head 7. The second ring-shaped seal 26 is arranged between the two surfaces 36 and 37 of the tubular part 8 and the nozzle head 7, which surfaces extend perpendicularly to the axis of rotation 15. In this case the ring plane 35 of the second ring-shaped seal 26 extends perpendicularly to the axis of rotation 15 of the nozzle head 7. In this embodiment the second ring-shaped seal 26 also provides an effective sealing between two nozzle-head inlets 24 and 25 which are off-centered from the axis of rotation 15 of the nozzle head 7, so that depending on the rotary position of the nozzle head 7 either only the first nozzle-head inlet 24 or only the second nozzle-head inlet 25 is in fluid-transmitting communication with the single tubular-part outlet 23 of the tubular part 8.

In the dental-jet device shown in FIGS. 5 and 6 it is also achieved by very simple means that the fluid supply to the central jet orifice and the fluid supply to the peripheral jet orifices of the nozzle head are effectively isolated from one another, thereby precluding an undesirable fluid discharge from any of the non-activated jet orifices of the nozzle head. Moreover, the dental-jet device shown in FIGS. 5 and 6 has a very simple construction of the mouthpiece and the nozzle head.

We claim:

1. A dental-jet device comprising a grip member and at least one mouthpiece, which mouthpiece is connectible to the grip member and comprises a tubular part having a fluid channel and a nozzle head mounted on the tubular part at the location of the free end of said tubular part so as to be rotatable about an axis of rotation between a central-jet position and a peripheral-jet position, which nozzle head has at least one central jet orifice and a plurality of peripheral jet orifices, a ring-shaped seal being interposed between the tubular part and the nozzle head to preclude an undesirable water discharge to the exterior of the mouthpiece, wherein the tubular part has a single tubular-part outlet which communicates with the fluid channel of the tubular part and which is off-centered from the axis of rotation of the nozzle head, the nozzle head having only two nozzle-head inlets, which are off-centered from the axis of rotation of the nozzle head and which are sealed from one another by means of a second ring-shaped seal acting between the tubular part and the nozzle head, the first nozzle-head inlet being in fluid-transmitting communication with the tubular-part outlet in the central-jet position of the nozzle head and the second nozzle-head inlet being in fluid-transmitting communication with the tubular-part outlet in the peripheral-jet position of the nozzle head and wherein the first nozzle-head inlet is in fluid-transmitting communication with the at least one central-jet orifice of the nozzle head and the second nozzle-head inlet is in fluid-transmitting communication with the peripheral-jet orifices of the nozzle head.

2. A dental-jet device as claimed in claim 1, wherein the second seal is arranged between surfaces of the tubular part and of the nozzle head, which surfaces extend parallel to the axis of rotation of the nozzle head, and the ring plane of the second seal is inclined relative to the axis of rotation of the nozzle head.

3. A mouthpiece for a dental-jet device, which mouthpiece comprises a tubular part having a fluid channel and a nozzle head mounted on the tubular part at the location of the free end of said tubular part so as to be rotatable about an axis of rotation between a central-jet position and a peripheral-jet position, which nozzle head has at least one central jet orifice and a plurality of peripheral jet orifices, a ring-shaped seal being interposed between the tubular part and the nozzle head to preclude an undesirable water discharge to the exterior of the mouthpiece, wherein the tubular part has a single tubular-part outlet which communicates with the fluid channel of the tubular part and which is off-centered from the axis of rotation of the nozzle head, the nozzle head having only two nozzle-head inlets, which are off-centered from the axis of rotation of the nozzle head and which are sealed from one another by means of a second ring-shaped seal acting between the tubular part and the nozzle head, the first nozzle-head inlet being in fluid-transmitting communication with the tubular-part outlet in the central-jet position of the nozzle head and the second nozzle-head inlet being in fluid-transmitting communication with the tubular-part outlet in the peripheral-jet position of the nozzle head and wherein the first nozzle-head inlet is in fluid-transmitting communication with the at least one central-jet orifice of the nozzle head and the second nozzle-head inlet is in fluid-transmitting communication with the peripheral-jet orifices of the nozzle head.

4. A mouthpiece as claimed in claim 3, wherein the second seal is arranged between surfaces of the tubular part and of the nozzle head, which surfaces extend parallel to the axis of rotation of the nozzle head, and the ring plane of the second seal is inclined relative to the axis of rotation of the nozzle head.

* * * * *